(12) United States Patent
Dozortsev et al.

(10) Patent No.: US 11,344,879 B2
(45) Date of Patent: May 31, 2022

(54) DEVICE FOR PROCESSING SPERM

(71) Applicants: Dmitri Dozortsev, Houston, TX (US); Michael Allon, Houston, TX (US)

(72) Inventors: Dmitri Dozortsev, Houston, TX (US); Michael Allon, Houston, TX (US)

( * ) Notice: Subject to any disclaimer, the term of this patent is extended or adjusted under 35 U.S.C. 154(b) by 154 days.

(21) Appl. No.: 16/666,619

(22) Filed: Oct. 29, 2019

(65) Prior Publication Data
US 2020/0391199 A1    Dec. 17, 2020

Related U.S. Application Data

(60) Provisional application No. 62/914,434, filed on Oct. 12, 2019, provisional application No. 62/879,602, filed on Jul. 29, 2019, provisional application No. 62/862,393, filed on Jun. 17, 2019.

(51) Int. Cl.
*B01L 3/00* (2006.01)
*A61B 17/43* (2006.01)

(52) U.S. Cl.
CPC ............ *B01L 3/502* (2013.01); *A61B 17/43* (2013.01); *B01L 2200/026* (2013.01); *B01L 2300/042* (2013.01); *B01L 2300/0832* (2013.01); *B01L 2300/0877* (2013.01); *B01L 2300/0883* (2013.01); *B01L 2300/168* (2013.01); *B01L 2400/049* (2013.01); *B01L 2400/06* (2013.01)

(58) Field of Classification Search
CPC ............ B01L 3/502; B01L 2300/0877; B01L 2300/042; B01L 2300/0832; B01L 2200/026; B01L 2300/168; B01L 2300/0883; B01L 2400/049; B01L 2400/06; A61B 17/43; A61B 10/0058; A61D 19/021; A61D 19/022
See application file for complete search history.

(56) References Cited

U.S. PATENT DOCUMENTS

| | | | |
|---|---|---|---|
| 8,486,353 B2 * | 7/2013 | Wu | B01L 3/502 422/557 |
| 2003/0027359 A1 * | 2/2003 | Hudak | B01L 3/502 436/518 |
| 2009/0100944 A1 * | 4/2009 | Newby | A61B 10/0096 73/864.63 |
| 2014/0007659 A1 * | 1/2014 | Yuan | G01N 33/493 73/61.41 |
| 2016/0051234 A1 * | 2/2016 | Gerdes | A61B 10/0038 422/547 |

* cited by examiner

*Primary Examiner* — Jill A Warden
*Assistant Examiner* — Dwayne K Handy
(74) *Attorney, Agent, or Firm* — Benjamin Aaron Adler

(57) ABSTRACT

Provided herein is a semen processing device. The device is a collection cup with a top portion encompassing a collection cavity into which the semen sample is deposited and a bottom portion encompassing a processing chamber and containing the processing unit for the collected semen. A flow control valve or a serpentine channel may be disposed as part of the processing unit to regulate the flow rate of semen from the collection cavity into the processing unit. A harvesting dock is disposed through the surface of the bottom portion. The semen flows from the collection cavity into the processing unit and is harvested through the harvesting dock.

27 Claims, 7 Drawing Sheets

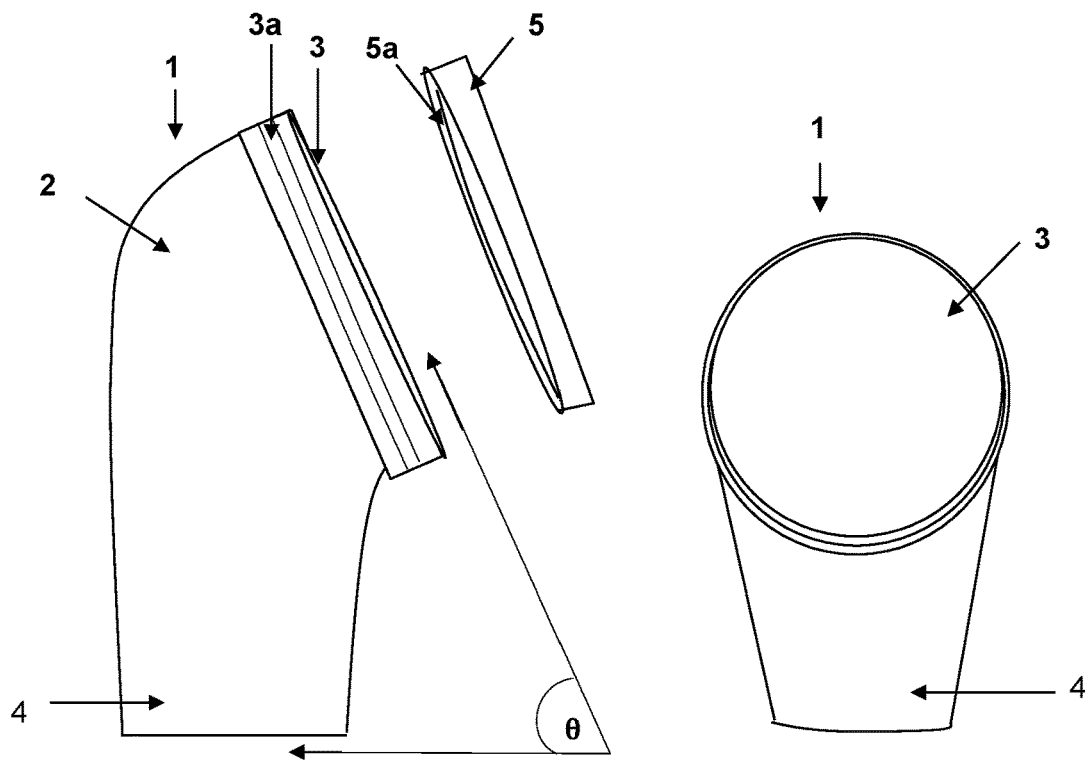
FIG. 1A
FIG. 1B
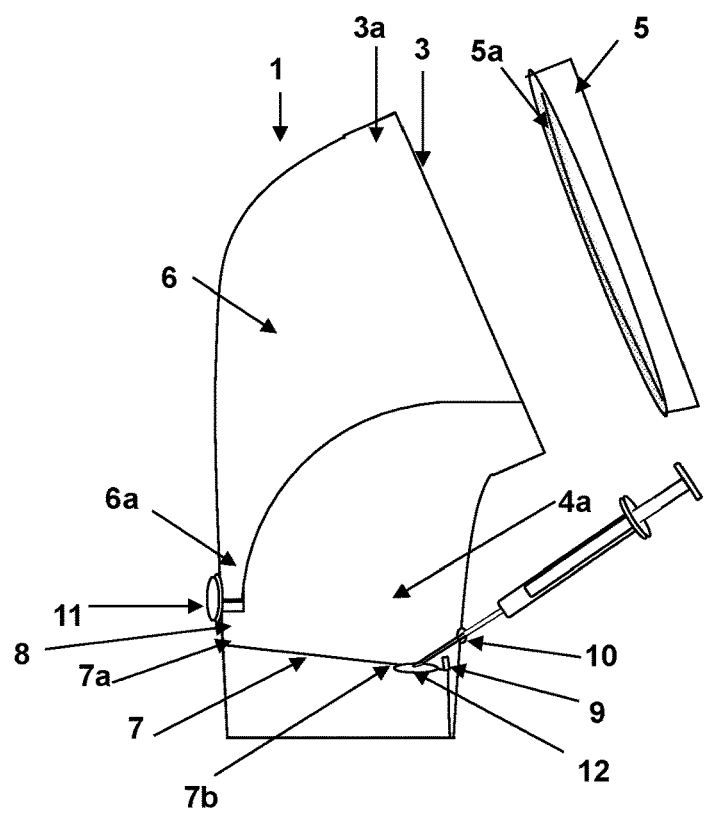
FIG. 1C

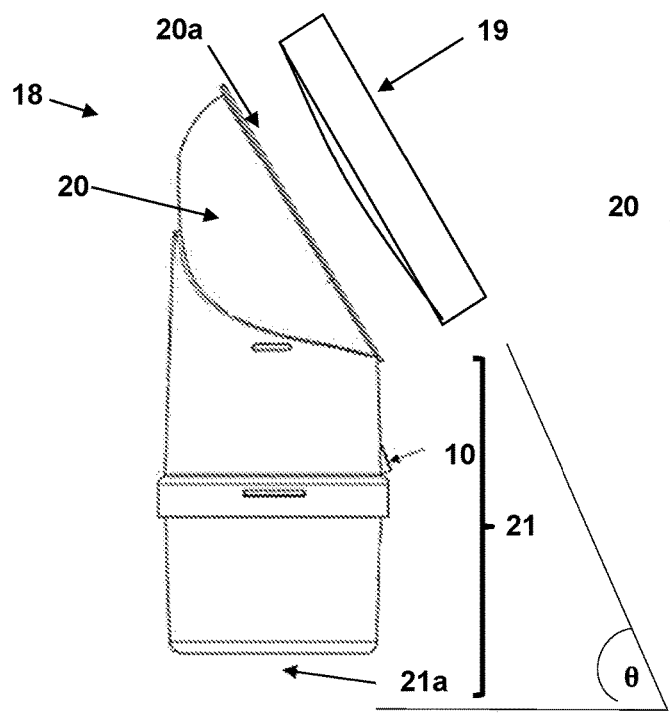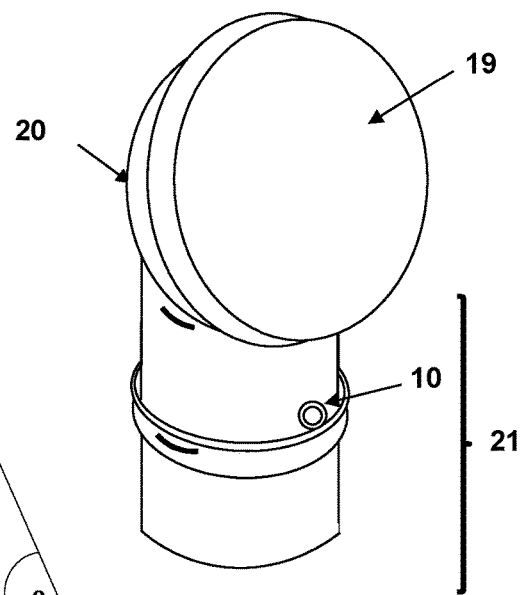
FIG. 4A    FIG. 4B
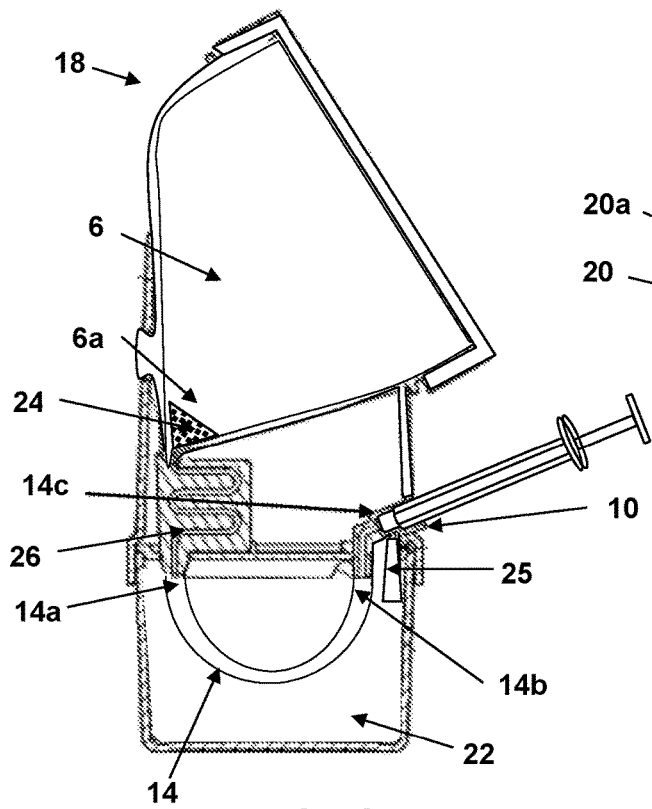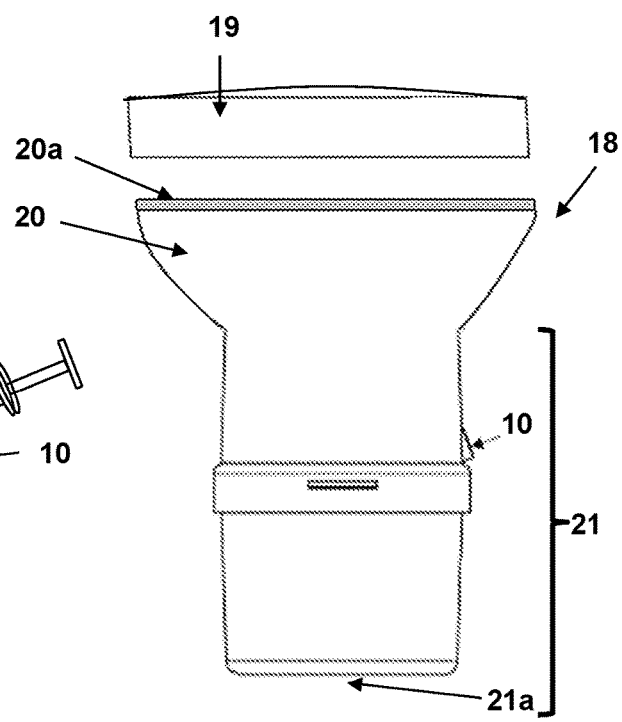
FIG. 4C    FIG. 4D

DEVICE FOR PROCESSING SPERM

CROSS-REFERENCE TO RELATED APPLICATIONS

This application claims benefit of priority under 35 U.S.C. § 119(e) of provisional applications U.S. Ser. No. 62/914,434, filed Oct. 12, 2019, U.S. Ser. No. 62/879,602, filed Jul. 29, 2019 and U.S. Ser. No. 62/862,393 filed Jun. 17, 2019, the entirety of all of which are hereby incorporated by reference.

BACKGROUND OF THE INVENTION

Field of the Invention

The invention relates to the fields of human fertility and assisted conception. More specifically, the present invention is directed to a device for processing a sperm sample before an assisted conception procedure.

Description of the Related Art

Assisted reproduction requires a sperm sample that has been processed to remove the bulk of the seminal plasma. Current methods for processing a sperm sample requires transfer of the semen sample from the collection container into a processing tube and separating and washing the sperm by centrifugation or similar methods. These methods require significant processing time and hands-on training, thereby limiting the job to a specialized laboratory. Furthermore, since most laboratories process several sperm samples a day, transferring to processing tubes followed by washing steps increases the risk of contamination and sample mix-up.

Thus, there is a deficiency in the art for devices for processing sperm in the shortest possible time. The present invention fulfills this longstanding need and desire in the art.

SUMMARY OF THE INVENTION

The present invention is directed to a device for collecting and processing a semen sample comprising a collection cup. The collection cup has a top portion and a bottom portion. The top portion has an open face and a downwardly tapered collection cavity with an open tapered distal end formed from the open face. The bottom portion is in fluid communication with the top portion and comprises a processing chamber formed there within. The processing chamber contains a processing unit disposed therein that is in communication with the collection cavity. A harvesting dock is disposed through a front surface of the bottom portion and is in fluid communication with the processing unit.

The present invention is directed to a related device that further comprises a filter at the open tapered distal end in the collection cavity. The present invention is directed to another related device that further comprises a cap removably engageable with the open face in the top portion of the collection cup.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A-1C show a first configuration for a semen processing device. FIG. 1A is a side view of the device in a vertical orientation showing a dome-shaped collection cup with a top portion and a bottom portion. FIG. 1B is a front view of the device shown in FIG. 1A showing the dome-shaped open face of the collection cup and the bottom. FIG. 1C is a cross-sectional view of the device in FIG. 1A, showing a collection cavity formed within the collection cup and a processing unit comprising an inclined plane in the bottom portion.

FIG. 2A is a perspective view of the inclined plane processing unit. FIG. 2B is a magnified view of the lower end of the inclined plane or ramp shown in FIG. 2A. FIG. 2C is an alternate configuration of the inclined plane with ridges on the top surface. FIG. 2D is a partial view of the inclined plane in FIG. 2C magnified to show the plurality of ridges.

FIG. 3A is a cross-sectional view of the device showing a collection cavity formed within the collection cup and a processing unit comprising a U-shaped processing duct. FIG. 3B is a magnified view of the second end of the U-shaped duct shown in FIG. 3A showing a circular ridge.

FIGS. 4A-4D shows a third configuration for the semen processing device. FIG. 4A is side view showing a dome-shaped collection cup attached to a bottom portion. FIG. 4B a left to right view of the semen processing device shown in FIG. 4A. FIG. 4C is a cross-sectional view of the device showing a collection cavity formed within the collection cup and a processing unit comprising a U-shaped processing duct. FIG. 4D is an alternative orientation of the dome-shaped collection cup attached to the bottom portion shown in FIG. 4A.

DETAILED DESCRIPTION OF THE PRESENT INVENTION

Figure 2A:
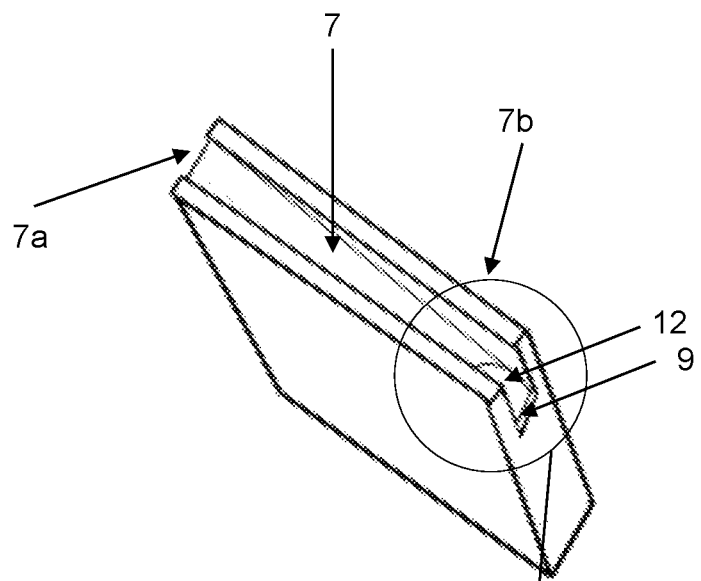
FIGS. 2A-2D show the features of the inclined plane or ramp in the semen processing device shown in FIG. 1C.

As used herein, the articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "including" is used herein to mean "including, but not limited to". "Including" and "including, but not limited to" are used interchangeably.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). For example, an angle measuring 0.9 degrees or 99 degrees at the intersection of the planes across the bottom surface of the bottom portion of the cup and across the open face of the top portion of the collection cup are considered within the scope of about 1 degree and about 90 degrees, respectively.

As used herein, the terms "collection cup", "cup", "device", and "semen processing device" are interchangeable.

As used herein, the terms "proximal" and "distal" in reference to the device refer to those components, features, parts and aspects thereof that are nearer or nearest to or farther or farthest from the open face on the top portion, respectively.

As used herein, the terms "front" and "back" in reference to the device refer to the side comprising the harvesting dock and the side opposite thereto, respectively.

As used herein, the term "processing unit" refers to a component or an arrangement of components within the processing chamber over and/or through which the semen sample and wash fluids and/or a medium pass during processing and prior to harvesting.

In one embodiment of the present invention there is provided a device for collecting and processing a semen sample, comprising a collection cup, comprising a top portion with an open face and a downwardly tapered collection cavity with an open tapered distal end formed from the open face; and a bottom portion in fluid communication with the top portion comprising a processing chamber formed therewithin; a processing unit disposed within the processing chamber and in fluid communication with the collection cavity; and a harvesting dock disposed through a front surface thereof in fluid communication with the processing unit.

Further to this embodiment the device comprises a filter disposed at the open tapered distal end in the collection cavity. In another further embodiment the device comprises a cap removably engageable with the open face in the top portion of the collection cup.

In all embodiments, the top portion may be substantially dome-shaped. In all embodiments, the bottom portion may be substantially cylindrical. In addition a plane across a bottom surface of the bottom portion may intersect a plane across the opening in the top portion at an angle of about 1 degree to about 90 degrees. Alternatively, a plane across a bottom surface of the bottom portion may be parallel to a plane across the opening in the top portion. Furthermore, the device may be made substantially of an optically transparent material.

In one aspect of all embodiments, the processing unit comprises a flow control valve disposed at the open tapered distal end of the collection cavity; an inclined plane transversely disposed in the processing chamber with an upper proximal end disposed below the flow control valve and in fluid communication with the open tapered distal end of the collection cavity when the flow control valve is in an open position, and a lower distal end downwardly inclined from the upper proximal end; and a recess formed on a top surface of the lower distal end accessible through the harvesting dock, said harvesting dock configured to removably receive a syringe therethrough to harvest sperm from the recess.

Further to this aspect the processing unit may comprise at least one ridge extending upwardly from the top surface of the inclined plane. In this further aspect the ridge may form an angle of less than 90 degrees with the inclined plane.

In all embodiments and aspects the inclined plane may form an angle from about 20 degrees to about 60 degrees with the plane across the bottom surface. The bottom portion may be optically transparent and is configured for optical alignment with a pair of viewing scopes comprising a cell counter at the upper proximal end of the inclined plane and at the recess formed at the lower distal end of the inclined plane.

In another aspect of all embodiments the processing unit comprises a processing duct with a first open end in fluid communication with the open tapered distal end of the collection cavity and a second open end in fluid communication with the harvesting dock, said harvesting dock configured to removably receive a syringe therethrough to harvest sperm from the processing duct; and a drain into the processing chamber disposed proximate to and in fluid communication with the harvesting dock. In this aspect, the processing duct may have a total inner surface area of about 2 $cm^2$ to about 10 $cm^2$.

Further to this aspect the processing unit may comprise a flow control valve disposed at the open tapered distal end of the collection cavity. Also further to this aspect the processing unit may comprise a serpentine channel disposed between the open tapered distal end of the collection cavity and the first end of the processing duct and in fluid communication therewith. Still further to this aspect the processing unit may comprise at least one ridge formed along an inner perimeter of the processing duct. In this further aspect the ridge may form an angle of less than 90 degrees with the inner surface of the processing duct.

In yet another aspect of all embodiments the processing unit comprises a receiving chamber with a first opening in fluid communication with the open tapered distal end of the collection cavity and a second opening in fluid communication with the harvesting dock; an aspiration tube depending from the second opening into the receiving chamber and in fluid communication therewith, said harvesting dock configured to removably receive a syringe therethrough to harvest sperm via the aspiration tube; and a drain into the processing chamber disposed proximate to and in fluid communication with the harvesting dock.

Further to this aspect the processing unit may comprise a flow control valve disposed at the open tapered distal end of the collection cavity. Further to this aspect the processing unit may comprise a serpentine channel disposed between the open tapered distal end of the collection cavity and the first opening into the receiving chamber and in fluid communication therewith.

In yet another aspect of all embodiments the processing unit comprises a chamber comprising a lower portion in fluid communication with the open tapered distal end of the collection cavity, an upper portion in fluid communication with the harvesting dock; and a porous membrane disposed transversely between the lower portion and the upper portion, said harvesting dock configured to removably receive a syringe therethrough to add clean fluid to the upper portion or to harvest sperm from the upper portion; and a drain into the processing chamber disposed proximate to and in fluid communication with the harvesting dock.

Further to this aspect the processing unit may comprise a flow control valve disposed at the open tapered distal end of the collection cavity. Further to this aspect the processing unit may comprise a serpentine channel disposed between the open tapered distal end of the collection cavity and the chamber and in fluid communication therewith.

In all embodiments and aspects the harvesting dock is configured to removably engage a pump. Particularly the pump may be a peristaltic pump.

Described herein is a device for collecting and processing semen for use in assisted conception or assisted reproduction. Generally, the device is a collection cup with a top portion for collection and a bottom portion for processing and harvesting. The top portion is in fluid communication with the bottom portion. The collection cup may have any shape and size suitable to receive a semen ejaculate from a penis. In a non-limiting example, the collection cup is substantially dome-shaped at the top portion. The bottom portion may have any suitable shape and size that enables a user to hold the collection cup with one hand or enables the cup to be clamped or otherwise secured, for example, to the arm of a chair or the edge of a table. The bottom portion may be substantially cylindrical. It is contemplated that the top portion and the bottom portion are separable units that are removably fastenable to each other. Removable fastening means may be by any commercially available means including, but not limited to, threading, clips, snaps or snap clamps.

A cap removably covers or removably engages the collection cup at the open face. Means for removably engaging or covering the collection cup are standard and known in the art. For example, the cap and the collection cup may be interiorly and exteriorly threaded, respectively, or the cap may snap onto the collection cup. Covering the open face keeps the interior of the cup clean prior to use and enables storage of the collected semen sample after use.

The collection cup has an open face on the top portion at the front that may be angled at an angle greater than zero with respect to the bottom surface of the bottom portion. This is beneficial since it enables the user to position the penis at the open face without having to tilt the collection cup. For example, the angle at the intersection of the plane across the open face with the plane across the bottom surface of the bottom portion may be about 1 degree to about 90 degrees. Alternatively, the open face may be parallel with the bottom portion. The interior arrangement of the top portion and the bottom portion remains the same for any angle.

The top portion encompasses a collection cavity accessed through the open face. The collection cavity tapers downwardly toward the bottom portion and forms or ends as an open tapered end distal to the open face through which the collected semen sample passes. This is beneficial since it reduces the surface area and concentrates the semen deposit within a small area above and before entering the bottom portion of the collection cup and further reduces evaporation. Optionally, flow may be further slowed or controlled with a flow control valve or serpentine channel fluidly connecting the top portion and the bottom portion. A filter may be optionally disposed in the collection cavity at the open tapered end. The filter prevents large cells from entering the bottom portion and blocking flow of the sperm.

The bottom portion forms a processing chamber therein. A processing unit is disposed within the processing chamber and is in fluid communication with the top portion and collects and processes sperm in the sample entering from the collection cavity. The processing unit has various configurations, including, but not limited to, an inclined plane, a processing duct, a flat receiving chamber and a chamber containing a porous membrane.

Particularly, the flow control valve or, alternatively, the serpentine channel, fluidly connects the collection cavity at the open tapered distal end and the processing unit and controls the flow rate of the semen into the processing unit. The processing unit and the open tapered distal end of the collection cup have a vertical separation of a suitable length that enables placement of either the flow control valve or the serpentine channel between the collection cavity and processing chamber to control semen flow rate to the processing unit. The vertical length may be from about 5 mm to about 20 mm. Particularly, the vertical separation between the processing unit and the open tapered distal end of the collection cup is 10 mm.

A harvesting dock is disposed through the front surface of the bottom portion in fluid communication with the processing unit. The processed sperm are harvested from the processing unit through the harvesting dock. The harvesting dock may comprise only an orifice or opening into the bottom portion. The orifice of the harvesting dock has a diameter sufficient to receive a syringe, with or without a needle attached, therethrough. Alternatively, the harvesting dock may comprise a connector formed from the orifice and extending into the processing chamber to fluidly connect with the processing unit. The harvesting dock may be made from any suitable material that permits forming an airtight seal around the syringe. Examples include, but are not limited to, silicone, nylon, polyethylene, polypropylene, vinyl and rubber. A combination of these materials also may be used.

In the connector configuration the harvesting dock may fluidly connect to a drain disposed to drain into the processing chamber. The drain enables draining of excess fluid, including wash and waste fluids, into the processing chamber instead of outside the device through the harvesting dock. The drain is positioned such that when a syringe is inserted into the harvesting dock, the syringe barrel seals the drain whereby wash fluids and/or media may be injected into the processing unit and processed sperm may be aspirated into the syringe instead of draining into the processing chamber.

The harvesting dock may be configured to removably attach a pump thereto. The pump enables clean medium or other clean fluid to be introduced into the processing chamber. Any commercially available pump that keeps the processed sample under sterile conditions may be used for this purpose. For example, the pump is a peristaltic pump.

The components of the collection cup independently may be made from any suitable inert biocompatible material to which the sperm will not attach or adhere. Examples include, but are not limited to, natural and synthetic polymers or polymer composites, or a combination of these materials. The components independently may be opaque, translucent or optically transparent.

Particularly, the bottom portion of the collection cup may be optically transparent thereby enabling a count of the total sperm and processed sperm using a cell counter with a pair of viewing scopes. For example, one viewing scope is optically aligned through the bottom portion proximate to the open tapered distal end of the collection cavity for a total sperm count. The other viewing scope is optically aligned through the bottom portion proximate to the sperm in the processing unit after processing for a count of processed sperm Particularly, embodiments of the present invention are better illustrated with reference to the Figure(s), however, such reference is not meant to limit the present invention in any fashion. The embodiments and variations described in detail herein are to be interpreted by the appended claims and equivalents thereof.

FIG. 1A is an exterior side view of the semen processing device showing a collection cup 1 with dome-shaped open top portion 2 with an open face 3 and a bottom portion 4. The top portion is exteriorly threaded at 3a, which enables a user to close the open top portion with a cap 5 interiorly threaded at 5a. The plane of the open face is disposed at an angle θ greater than 0° and less than 90° with respect to the plane across the bottom 4. Alternatively, the plane across the open face on the collection cup may be parallel (see FIG. 4D) with the plane across the bottom.

With continued reference to FIG. 1A, FIG. 1B is a front view of the collection cup showing the open face 3 and the bottom portion 4.

With continued reference to FIG. 1A, FIG. 1C is a cross-sectional view of the collection cup 1, showing the processing chamber 4a formed in the bottom portion. A collection cavity 6 formed in the top portion tapers downwardly to an open tapered distal end 6a and is in fluid communication with the upper proximal end 7a of the inclined plane 7 such that a space 8 is formed between the open tapered distal end and the upper end of the inclined plane. The inclined plane is substantially smooth on the top surface to enable flow of the semen by gravity from the upper proximal end to the recess at the lower distal end. The inclined plane is angled at any suitable angle with the plane across the bottom portion which would enable flow of the semen by gravity. For example the inclined plane is disposed at an angle from about 30 degrees to about 45 degrees with the plane across the bottom.

A flow control valve 11 is disposed through the back surface of the bottom portion and extends into space 8 to control the flow of the semen from the collection cavity to the upper end of the inclined plane. A recess 12 is formed at the lower distal end 7b of the inclined plane 7. The recess is a shallow depression on the surface of the inclined plane and enables the processed semen to be collected before it is harvested.

A ridge 9 extends upwardly from the surface across the width of the inclined plane at the lower distal end. The ridge may be formed at an angle less than 90 degrees with the inclined plane. The ridge may have a height from about 2 mm to about 4 mm. For example, the ridge height is 3 mm. Alternatively, a plurality of ridges 17 (see FIG. 2C) are added and are formed or disposed in parallel down the length of the inclined plan. The plurality of ridges 17 controls flow of the semen down the inclined plane to the recess and the ridge 9 prevents loss of the processed semen due to overflow. A harvesting dock 10 is disposed through the front surface of the bottom portion enables a user to insert a syringe with needle into the processing chamber and aspirate the processed sperms from the recess formed on the inclined plane.

With continued reference to FIG. 1C, FIG. 2A is a magnified view of the inclined plane 7 showing the upper proximal end 7a and the lower distal end 7b. The recess 12 is formed at the lower distal end of the inclined plane for collecting the processed semen. The ridge 9 is formed on the surface of the inclined plane across its width.

Figure 2B:
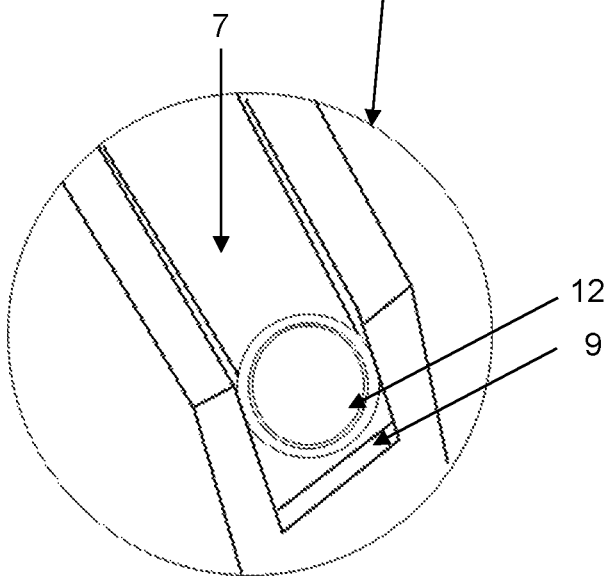
Figure 2C:
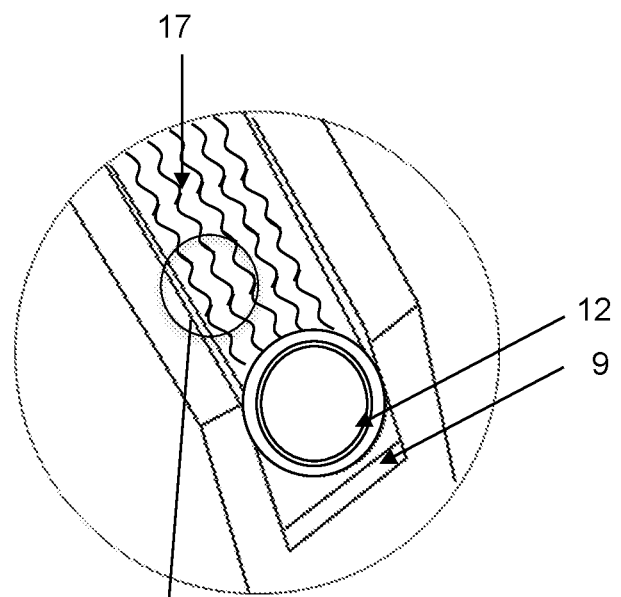
Figure 2D:
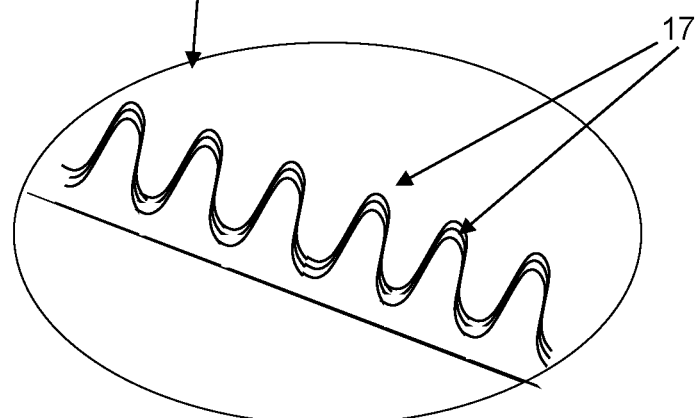

With continued reference to FIGS. 1C and 2A, FIG. 2B is a magnified view of the lower distal end 7b of the inclined plane 7 showing the circular recess 12 and ridge 9 formed across the width of the inclined plane.

With continued reference to FIGS. 1C, 2A and 2B, 2C is a magnified view of the lower distal end 7b of the inclined plane with the circular recess 12 and ridge 9 formed across the width of the inclined plane. A plurality of ridges 17 are formed on the surface of the inclined plane along its length in parallel.

With continued reference to FIGS. 1C and 2A-2C, 2D is a magnified cross-sectional view through the inclined plane illustrating the disposition of the ridges 17 on the surface of the inclined plane.

Figure 3A:
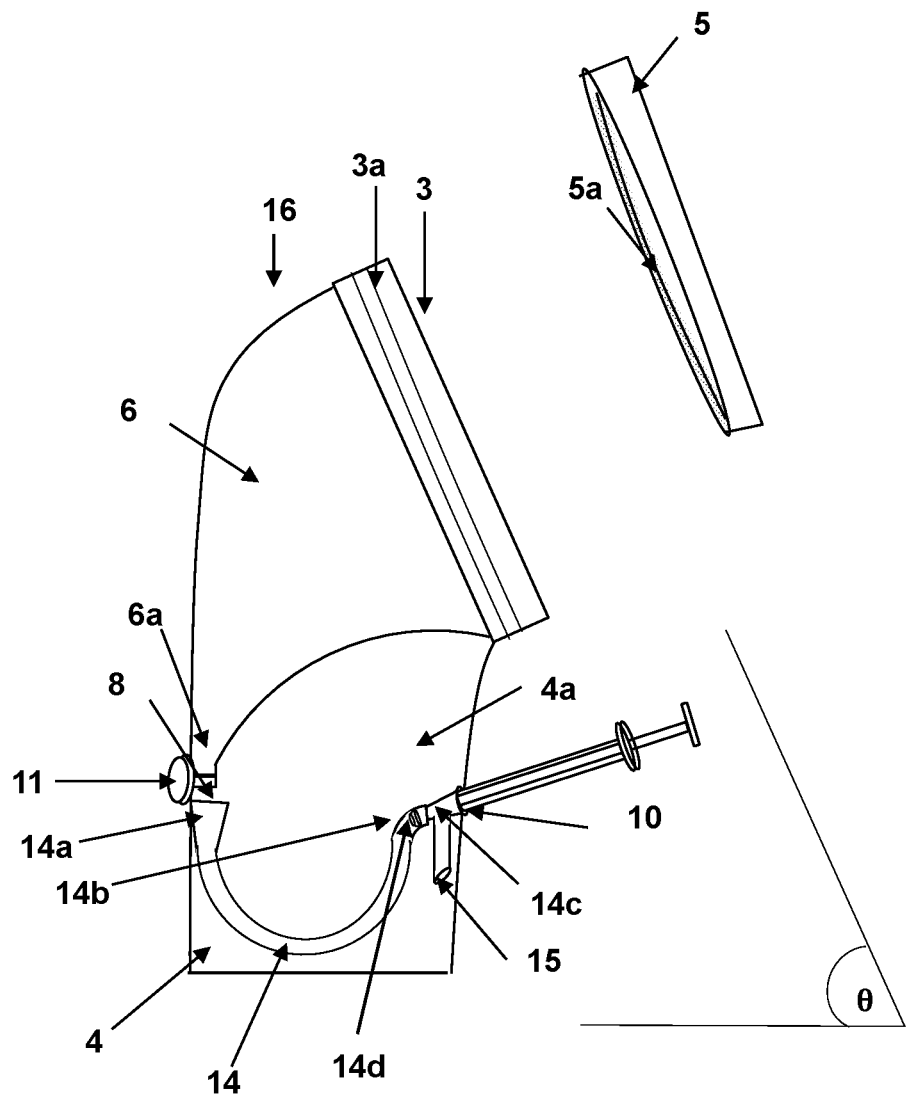
FIGS. 3A-3B shows a second configuration for the semen processing device.

With continued reference to FIGS. 1A and 1B, FIG. 3A is a cross-sectional view of a collection cup 16 illustrating a second configuration of the processing unit. The collection cup has a dome-shaped top portion 2 and a bottom portion 4. The components within the top portion of the collection cup and the cap 3 and the arrangement thereof are the same as in FIG. 1C including the open face 3 and exterior threads 3a thereon on the top portion, the cap 5 interiorly threaded at 5a, the downwardly tapering collection cavity 6 with the open tapered distal end 6a.

The bottom portion forms the processing chamber 4a with the processing unit that is a substantially U-shaped processing duct 14 disposed therein although the processing duct may have any suitable shape and size that enables flow of the semen sample within its internal space, for example cylindrical or tubular. The processing duct may have a total internal surface area of about 10 cm². The flow control valve 11 extends into the space 8 formed beneath the open tapered distal end. The open tapered distal end is in fluid communication with the first open end 14a of the processing duct across the space 8. The second open end 14b of the processing duct is fluidly connected to the harvesting dock 10.

The processing duct is substantially smooth on an inner surface to enable smooth flow of the semen. Alternatively, a circular ridge 14c is formed on an inner surface of the processing duct to control the flow of semen and wash medium or fluid during processing. It is contemplated that the ridge may have a non-circular shape. The circular or non-circular ridge conforms to the shape of the processing duct and is disposed around an inner perimeter therein. The ridge controls flow of the semen inside the processing duct. The ridge may be formed at an angle of less than 90 degrees with the inner surface of the processing duct. The ridge may have a height of about 2 mm to about 4 mm. For example, the ridge may have a height of about 3 mm.

A drain 15 proximate to and fluidly connected with the harvesting dock extends downwardly into the processing chamber. The drain enables draining of excess fluid, including wash and waste fluids, into the processing chamber, instead of outside the collection cup. The drain is configured such that when a syringe is inserted into the harvesting dock 10, the syringe barrel seals the drain whereby processed semen may be aspirated into the syringe instead of flowing into the processing chamber.

Figure 3B:
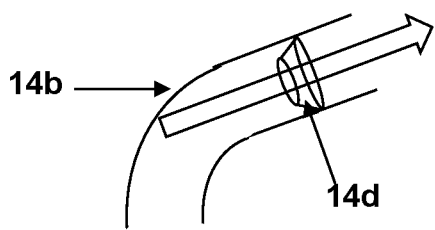

With continued reference to FIG. 3A, FIG. 3B is a magnified view of the second open end 14b of the processing duct showing the circular ridge 14d circumferentially disposed around an inner surface thereof to control flow rates.

FIG. 4A an exterior side view of another configuration of the semen processing device showing a collection cup 18 that has a dome-shaped top portion 20 and a bottom portion 21. The top portion comprises an open face 20a, which may be closed with cap 19. The harvesting dock 10 is disposed through the front of the bottom portion as in FIG. 1C. The plane across the open top 20a is disposed at an angle θ greater than 0° and less than 90° with respect to the plane of the base 21a of the bottom portion 21. It is contemplated that the top portion may be removably secured to the bottom portion, for example, by threadably engaging the top portion to the bottom portion or by snapping or clipping one portion to the other.

With continued reference to FIG. 4A, FIG. 4B is a perspective view of the collection cup 18 showing the harvesting dock 10 and the cap 19 covering the open face 20a of the top portion 20.

With continued reference to FIGS. 3C, 4A and 4B, FIG. 4C is cross-sectional view of the collection cup 18 illustrating a third configuration for the processing unit. The collection cup is shown with the cap 19 on the top portion 20. The processing unit, a processing duct 14 is disposed within the processing chamber 22. The top portion forms the collection cavity 6 and has a filter 24 removably placed within the collection cavity at the open tapered distal end 6a to exclude large cells from entering and clogging the processing duct. A serpentine channel 26, fluidly connects the open tapered distal end with the first end 14a of the processing duct, enabling movement of the semen sample and washing fluids from the collection cavity to the processing duct. The second end 14b of the processing duct is attached to the harvesting dock 10. A user may insert a syringe into the harvesting dock to harvest or aspirate the processed semen. A drain 25 proximate to and fluidly connected with the harvesting dock extends downwardly into the processing chamber.

With continued reference to FIG. 4A, FIG. 4D is an alternative configuration of the collection cup where the plane across the open top 20a on the top portion 20 is parallel with the plane across the bottom 21a in the bottom portion 21. This is equivalent to an angle of 0 degrees.

Figure 5:
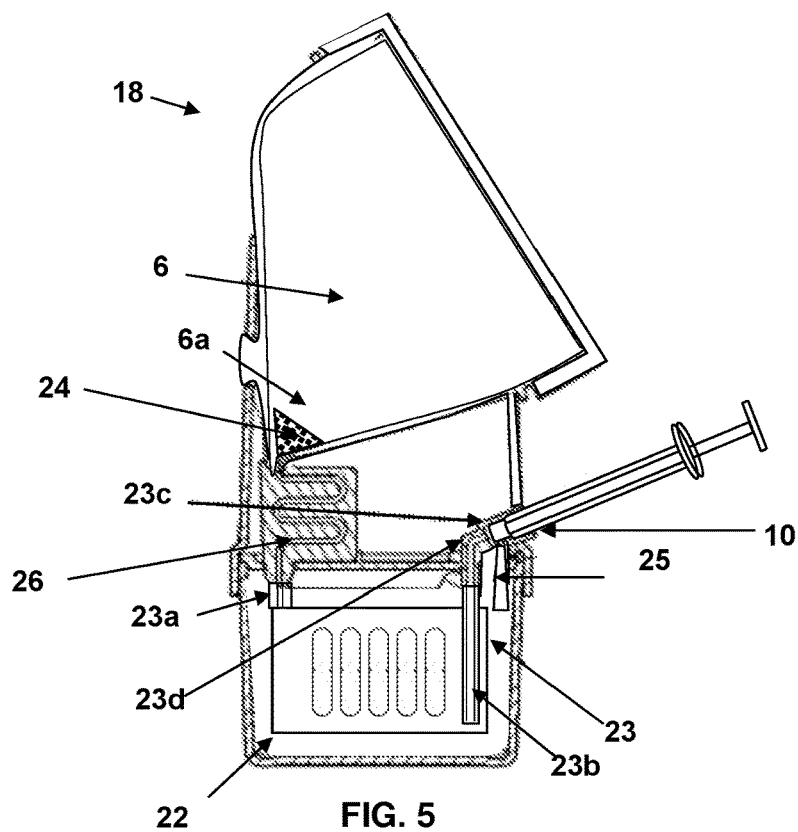
FIG. 5 is cross-sectional view of a fourth configuration for the semen processing device showing a collection cavity formed within the collection cup and a processing unit comprising a receiving chamber.

With continued reference to FIGS. 4A and 4B, FIG. 5 is a cross-sectional view of the collection cup 18 illustrating a fourth configuration for the processing unit. The collection cup is shown with the cap 19 on the top portion 20. The processing unit, a substantially flat receiving chamber 23 is disposed within the processing chamber 22. The receiving chamber may have any suitable substantially flat shape and size that enables flow of the semen sample within its internal space. The receiving chamber may have a distance between opposing walls of about 2 mm and a total surface area of about 10 mm$^2$. The receiving chamber may be substantially smooth on an inner surface.

The top portion forms the collection cavity 6 and has a filter 24 removably placed within the collection cavity at the open tapered distal end 6a to exclude large cells from entering and clogging the processing duct. A serpentine channel 26, fluidly connects the open tapered distal end with the first opening 23a of the substantially flat receiving chamber 23, enabling movement of the semen sample and washing fluids from the collection cavity to the receiving chamber. An upwardly directed aspiration tube 23b is disposed within the receiving chamber at a second end 23d. The aspiration tube is disposed in fluid communication with the harvesting dock 10 through which a user may insert a syringe to harvest or to aspirate the processed semen from the aspiration tube. A drain 25 proximate to and fluidly connected with the harvesting dock extends downwardly into the processing chamber.

Figure 6:
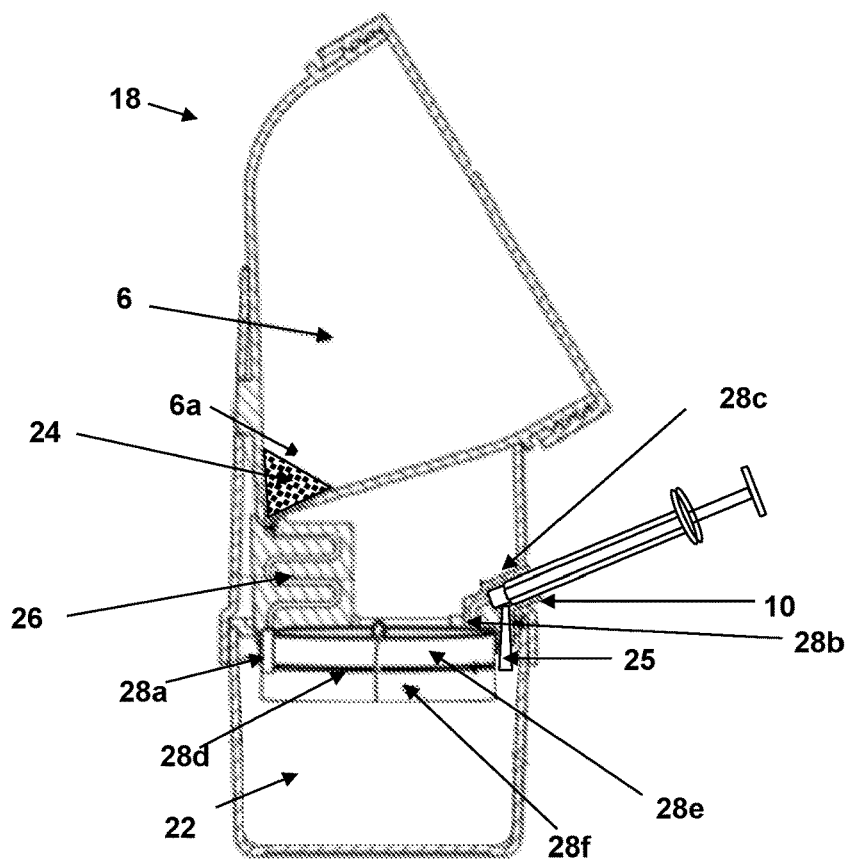
FIG. 6 is cross-sectional view of a fifth configuration for the semen processing device showing a collection cavity formed within the collection cup and a processing unit comprising a chamber divided into upper and lower portion by a porous membrane.

With continued reference to FIGS. 4A and 4B, FIG. 6 is a cross-sectional view of the collection cup 18 illustrating a fifth configuration for the processing unit. The collection cup is shown with the cap 19 on the top portion 20. The processing unit, a chamber 28 is disposed within the processing chamber 22. The chamber is divided by a porous membrane 28c transversly disposed therewithin to divide the chamber into an upper portion 28d and a lower portion 28e. The porous membrane may have a pore size through which sperm may migrate but which prevents large cells and debris in the semen sample from passing through the membrane.

A filter 24 is removably placed within the collection cavity 6 at the open tapered distal end 6a to exclude large cells from entering and clogging the processing duct. The serpentine channel 26 fluidly connects the open tapered distal end with the lower portion 28e of the chamber 28 through tube 28a enabling movement of the semen sample and washing fluids from the collection cavity into the lower portion. The upper portion 28d is in fluid communication with the harvesting dock 10 at 28b. A syringe is inserted into the harvesting dock to either introduce fresh, clean medium or clean fluid into the upper portion of the chamber during processing or to harvest or aspirate the sperm after their migration from the lower portion of the chamber through the porous membrane into the clean medium in the upper portion of the chamber. A drain 25 proximate to and fluidly connected with the harvesting dock extends downwardly into the processing chamber.

Figure 7:
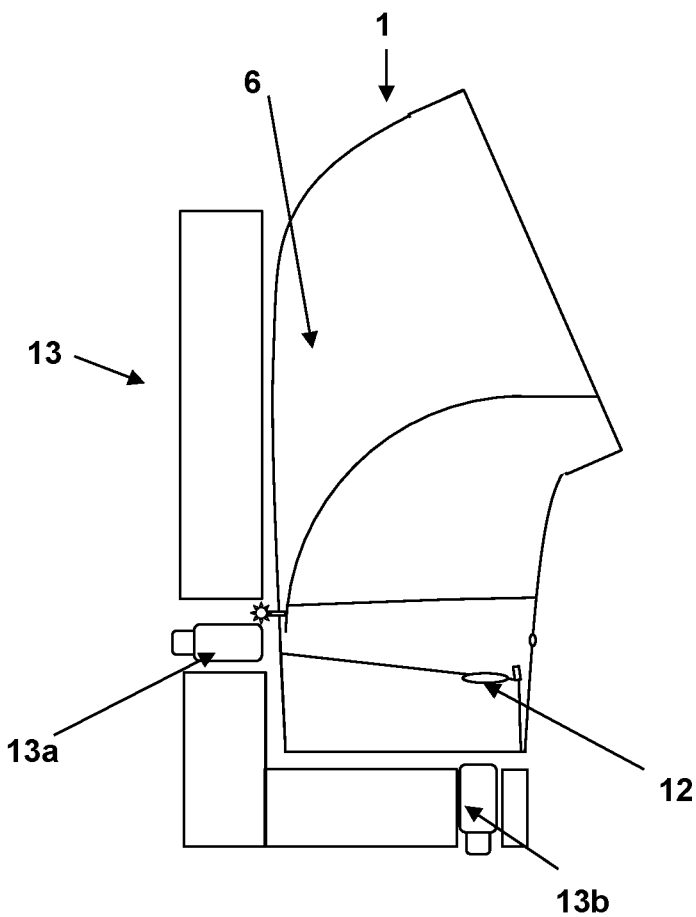
FIG. 7 shows illustrates the semen processing device in combination with a sperm cell counter.

FIG. 7 shows the collection cup 1 in combination with a sperm cell counter 13. The sperm cell counter comprises a horizontal viewing scope 13a optically aligned with the open tapered distal end 6. The horizontal viewing scope enables the user to perform a total sperm count in the semen sample before processing. The sperm cell counter also comprises a vertical viewing scope 13b disposed below and in optical alignment with the recess 12 on the lower distal end of the inclined plane. The vertical viewing scope enables the user to perform a count of processed sperm, i.e., after the semen is processed. By counting the sperm using the horizontal viewing scope and the vertical viewing scope the user can calculate percent recovery and sperm density in the processed sample which would be useful for calculating optimal sperm to egg ratios for in vitro fertilization.

What is claimed is:
1. A device for collecting and processing a semen sample, comprising:
    a collection cup, comprising:
        a top portion with an open face and a downwardly tapered collection cavity with an open tapered distal end formed from the open face;
        a bottom portion in fluid communication with the top portion comprising:
            a processing chamber formed therewithin;
            a harvesting dock disposed through a front surface of the bottom portion and configured to removably receive a syringe therethrough; and
            a processing unit disposed within the processing chamber and in fluid communication with the collection cavity, comprising
                a processing duct with a first open end in fluid communication with the open tapered distal end of the collection cavity and a second open end in fluid communication with the harvesting dock to harvest sperm from the processing duct via the syringe; and a drain into the processing chamber disposed proximate to and in fluid communication with the harvesting dock; and a flow control valve disposed at the open tapered distal end of the collection cavity.

2. The device of claim 1, further comprising a filter disposed at the open tapered distal end in the collection cavity.

3. The device of claim 1, further comprising a cap removably engageable with the open face in the top portion of the collection cup.

4. The device of claim 1, further comprising a serpentine channel disposed between the open tapered distal end of the collection cavity and the first end of the processing duct and in fluid communication therewith.

5. The device of claim 1, further comprising at least one ridge formed along an inner perimeter of the processing duct.

6. The device of claim 5, wherein the ridge forms an angle of less than 90 degrees with the inner surface of the processing duct.

7. The device of claim 1, wherein the processing duct has a total inner surface area of about 10 cm$^2$.

8. The device of claim 1, wherein the top portion is substantially dome-shaped.

9. The device of claim 1, wherein the bottom portion is substantially cylindrical.

10. The device of claim 1, wherein a plane across a bottom surface of the bottom portion intersects a plane across the opening in the top portion at an angle of about 1 degree to about 90 degrees or the plane across the bottom surface of the bottom portion is parallel to the plane across the opening in the top portion.

11. The device of claim 1, wherein the device is made substantially of an optically transparent material.

12. A device for collecting and processing a semen sample, comprising:
a collection cup, comprising:
a top portion with an open face and a downwardly tapered collection cavity with an open tapered distal end formed from the open face;
a bottom portion in fluid communication with the top portion comprising:
a processing chamber formed therewithin;
a harvesting dock disposed through a front surface of the bottom portion and configured to removably receive a syringe therethrough; and
a processing unit disposed within the processing chamber and in fluid communication with the collection cavity, comprising:
a receiving chamber with a first opening in fluid communication with the open tapered distal end of the collection cavity and a second opening in fluid communication with the harvesting dock;
a serpentine channel disposed between the open tapered distal end of the collection cavity and the first opening into the receiving chamber and in fluid communication therewith;
an aspiration tube extending upwardly from the second opening into the receiving chamber and in fluid communication therewith to harvest sperm from the aspiration tube via the syringe; and
a drain into the processing chamber disposed proximate to and in fluid communication with the harvesting dock; and a flow control valve disposed at the open tapered distal end of the collection cavity.

13. The device of claim 12, further comprising a filter disposed at the open tapered distal end in the collection cavity.

14. The device of claim 12, further comprising a cap removably engageable with the open face in the top portion of the collection cup.

15. The device of claim 12, wherein the top portion is substantially dome-shaped.

16. The device of claim 12, wherein the bottom portion is substantially cylindrical.

17. The device of claim 12, wherein a plane across a bottom surface of the bottom portion intersects a plane across the opening in the top portion at an angle of about 1 degree to about 90 degrees or the plane across the bottom surface of the bottom portion is parallel to the plane across the opening in the top portion.

18. The device of claim 12, wherein the device is made substantially of an optically transparent material.

19. A device for collecting and processing a semen sample, comprising:
a collection cup, comprising:
a top portion with an open face and a downwardly tapered collection cavity with an open tapered distal end formed from the open face;
a bottom portion in fluid communication with the top portion comprising:
a processing chamber formed therewithin;
a harvesting dock disposed through a front surface of the bottom portion and configured to removably receive a syringe therethrough; and
a processing unit disposed within the processing chamber and in fluid communication with the collection cavity, comprising:
a chamber comprising a lower portion in fluid communication with the open tapered distal end of the collection cavity, an upper portion in fluid communication with the harvesting dock to add clean fluid to the upper portion via the syringe or to harvest sperm from the upper portion via the syringe;
a serpentine channel disposed between the open tapered distal end of the collection cavity and the chamber and in fluid communication therewith;
a porous membrane disposed transversely between the lower portion and the upper portion; and
a drain into the processing chamber disposed proximate to and in fluid communication with the harvesting dock; and
a flow control valve disposed at the open tapered distal end of the collection cavity.

20. The device of claim 19, further comprising a filter disposed at the open tapered distal end in the collection cavity.

21. The device of claim 19, further comprising a cap removably engageable with the open face in the top portion of the collection cup.

22. The device of claim 19, wherein the harvesting dock is configured to removably engage a pump.

23. The device of claim 22, wherein the pump is a peristaltic pump.

24. The device of claim 19, wherein the top portion is substantially dome-shaped.

25. The device of claim 19, wherein the bottom portion is substantially cylindrical.

26. The device of claim 19, wherein a plane across a bottom surface of the bottom portion intersects a plane across the opening in the top portion at an angle of about 1 degree to about 90 degrees or the plane across the bottom surface of the bottom portion is parallel to the plane across the opening in the top portion.

27. The device of claim 19, wherein the device is made substantially of an optically transparent material.

* * * * *